(12) United States Patent
Ernst et al.

(10) Patent No.: US 7,365,210 B2
(45) Date of Patent: Apr. 29, 2008

(54) METHOD FOR THE PRODUCTION OF CHIRAL IMIDAZOLIDIN-2-ONES

(75) Inventors: Hansgeorg Ernst, Speyer (DE); Jürgen Koppenhöfer, Neustadt (DE); Daniela Klein, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 572 days.

(21) Appl. No.: 10/510,439

(22) PCT Filed: Apr. 8, 2003

(86) PCT No.: PCT/EP03/03615

§ 371 (c)(1),
(2), (4) Date: Oct. 7, 2004

(87) PCT Pub. No.: WO03/084933

PCT Pub. Date: Oct. 16, 2003

(65) Prior Publication Data

US 2005/0165078 A1 Jul. 28, 2005

(30) Foreign Application Priority Data

Apr. 11, 2002 (DE) ............... 102 15 845

(51) Int. Cl.
*C07D 233/04* (2006.01)
(52) U.S. Cl. ............... 548/311.1; 548/316.4
(58) Field of Classification Search ............. 548/311.1, 548/316.4
See application file for complete search history.

(56) References Cited

FOREIGN PATENT DOCUMENTS

WO        01/04098        1/2001

OTHER PUBLICATIONS

Ephedrine-Derived Imidazolidin 2 Ones, X_002931874, Bd. 126, pp. 2663-2673.

Close in J. Org. Chem., 15, 1131-1134 (1950).

*Primary Examiner*—Kamal A. Saeed
(74) *Attorney, Agent, or Firm*—Novak Druce + Quigg LLP

(57) ABSTRACT

The invention relates to a process for preparing chiral imidazolidin-2-ones of the formula I

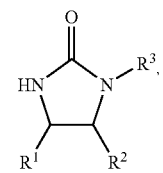
(I)

in which
$R^1$ is $C_1$-$C_8$-alkyl, cyclohexyl, phenyl, a $C_1$-$C_6$-alkyl-, halo-, nitro-, $C_1$-$C_6$-alkoxy-, $C_1$-$C_6$-alkylmercapto- or $CF_3$-substituted phenyl radical, naphthyl or a $C_1$-$C_6$-alkyl-, halo-, nitro-, $C_1$-$C_6$-alkoxy- or $CF_3$-substituted naphthyl radical,
$R^2$ is $C_1$-$C_8$-alkyl, $C_2$-$C_8$-alkenyl, cyclohexyl, phenyl or a phenyl-$C_1$-$C_6$-alkyl radical which may be substituted by a nitro, $C_1$-$C_6$-alkoxy, methylenedioxy or $CF_3$ radical, and
$R^3$ is $C_1$-$C_{12}$-alkyl, $C_2$-$C_8$-alkenyl, cyclohexyl, phenyl or a $C_1$-$C_6$-alkyl-, halo-, nitro-, $C_1$-$C_6$-alkoxy-, methylenedioxy-, dialkylamino- or $CF_3$-substituted phenyl radical,
by reacting a compound of the formula II or the salt thereof

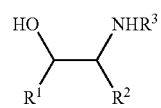
(II)

in which $R^1$, $R^2$ and $R^3$ have the abovementioned meaning, with urea in the presence of an involatile ammonium salt, wherein the reaction is carried out in the presence of an aprotic polar organic solvent.

9 Claims, No Drawings

METHOD FOR THE PRODUCTION OF CHIRAL IMIDAZOLIDIN-2-ONES

This application is a national stage filing under 35 U.S.C. § 371 of PCT International Application PCT/EPO3/036 15, filed Apr. 08, 2003 which claims priority under 35 U.S.C. 119 GERMANY 102158452 filed Apr. 11, 2002.

The present invention relates to an improved process for preparing chiral imidazolidin-2-ones of the general formula I

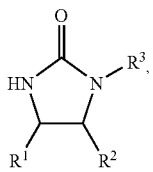

in which
$R^1$ is $C_1$-$C_8$-alkyl, cyclohexyl, phenyl, a $C_1$-$C_6$-alkyl-, halo-, nitro-, $C_1$-$C_6$-alkoxy-, $C_1$-$C_6$-alkylmercapto- or $CF_3$-substituted phenyl radical, naphthyl or a $C_1$-$C_6$-alkyl-, halo-, nitro-, $C_1$-$C_6$-alkoxy- or $CF_3$-substituted naphthyl radical,
$R^2$ is $C_1$-$C_8$-alkyl, $C_2$-$C_8$-alkenyl, cyclohexyl, phenyl or a phenyl-$C_1$-$C_6$-alkyl radical which may be substituted by a nitro, $C_1$-$C_6$-alkoxy, methylenedioxy or $CF_3$ radical, and
$R^3$ is $C_1$-$C_{12}$-alkyl, $C_2$-$C_8$-alkenyl, cyclohexyl, phenyl or a $C_1$-$C_6$-alkyl-, halo-, nitro-, $C_1$-$C_6$-alkoxy-, methylenedioxy-, dialkylamino- or $CF_3$-substituted phenyl radical, by reacting a compound of the formula II

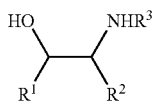

with urea in the presence of an ammonium salt.

The preparation of chiral imidazolidin-2-ones, which represent important intermediates in asymmetric synthesis, especially of bioactive compounds, is known per se.

Of particular importance in this connection are phenyl-substituted derivatives obtained by condensation of ephedrine with urea.

Thus, Close describes, in J. Org. Chem., 15, 1131-1134 (1950), the preparation of 1,5-dimethyl-4-phenylimidazolidin-2-one by condensation of D,L-ephedrine hydrochloride and pseudoephedrine with urea in the melt. Drewes et al., Chem. Ber., 126, 2663-2673 (1993), describe the preparation of the corresponding (4R,5S) enantiomer likewise by condensation of L(−)-ephedrine with urea in the melt.

However, the disadvantage of this method is the relatively high proportion of oxazolidinone as byproduct with, correspondingly, unsatisfactory yields of the imidazolidinone.

WO 01/04098 discloses a process for preparing chiral imidazolidin-2-ones by condensation of β-amino alcohols with urea in the presence of an involatile ammonium salt. Thus, for example, L-ephedrine can be converted into the corresponding 4-phenylimidazolidin-2-one as described in the reaction scheme below.

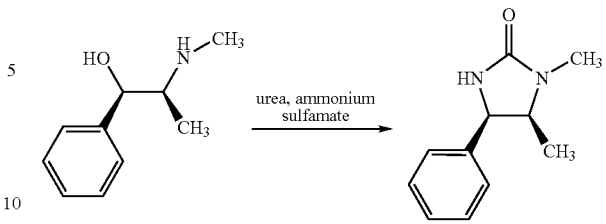

This entails the starting materials initially being mixed, using toluene as mixing aid, then distilling out the toluene and carrying out the reaction in the melt with evolution of ammonia.

The disadvantage in this case is, inter alia, the copious evolution of ammonia. The crude product obtained in this way is moreover still unsatisfactory in relation to purity and yield.

It is an object of the present invention to find an improved process which leads in a simple manner to good yields of products of high purity.

We have found that this object is achieved by a process for preparing chiral imidazolidin-2-ones of the general formula I

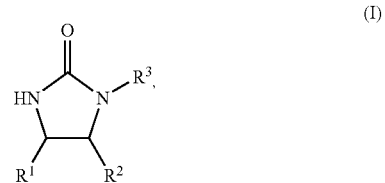

in which
$R^1$ is $C_1$-$C_8$-alkyl, cyclohexyl, phenyl, a $C_1$-$C_6$-alkyl-, halo-, nitro-, $C_1$-$C_6$-alkoxy-, $C_1$-$C_6$-alkylmercapto- or $CF_3$-substituted phenyl radical, naphthyl or a $C_1$-$C_6$-alkyl-, halo-, nitro-, $C_1$-$C_6$-alkoxy- or $CF_3$-substituted naphthyl radical,
$R^2$ is $C_1$-$C_8$-alkyl, $C_2$-$C_8$-alkenyl, cyclohexyl, phenyl or a phenyl-$C_1$-$C_6$-alkyl radical which may be substituted by a nitro, $C_1$-$C_6$-alkoxy, methylenedioxy or $CF_3$ radical, and
$R^3$ is $C_1$-$C_{12}$-alkyl, $C_2$-$C_8$-alkenyl, cyclohexyl, phenyl or a $C_1$-$C_6$-alkyl-, halo-, nitro-, $C_1$-$C_6$-alkoxy-, methylenedioxy-, dialkylamino- or $CF_3$-substituted phenyl radical, by reacting a compound of the formula II or the salt thereof

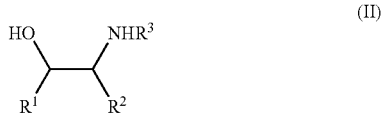

in which $R^1$, $R^2$ and $R^3$ have the abovementioned meaning, with urea in the presence of an ammonium salt, wherein the reaction is carried out in the presence of a polar organic solvent.

An aprotic polar solvent is preferably employed, and N-methylpyrrolidone is particularly preferably employed.

In a further preferred embodiment, the reaction takes place in the presence of a proton donor.

It is preferred for $R^1$ to be phenyl and $R^2$ and $R^3$ to be methyl, i.e. 1R,2S-ephedrine, 1S,2R-ephedrine, 1R,2R-pseudoephedrine or 1S,2S-pseudoephedrine or salts thereof are preferably employed. Suitable salts are, in particular, the hydrochlorides. 1R,2S-ephedrine, 1S,2R-ephedrine and the corresponding hydrochlorides are very particularly preferred.

The reaction takes place in the presence of ammonium salts. Suitable ammonium salts are those of mineral acids, of mineral acid derivatives such as sulfamic acid or ammonium salts of saturated $C_1$-$C_6$-carboxylic acids.

Examples of suitable ammonium salts are ammonium sulfamate, ammonium sulfate, diammonium hydrogen phosphate, ammonium dihydrogen phosphate or ammonium acetate, preferably inorganic ammonium salts, with particular preference for ammonium sulfamate. The ammonium salt is employed in amounts of from 0.5 to 3 equivalents, preferably 0.9 to 1.1 equivalents.

Urea is employed in amounts of from 1 to 5 equivalents, preferably 2.5 to 3.5 equivalents.

The reaction preferably takes place in the presence of a proton-donating compound. Suitable proton donors are strong acids, preferably with a $pK_a$ of <3, for example mineral acids such as sulfuric acid, phosphoric acid, hydrochloric acid or sulfuric acid derivates such as sulfamic acid, and organic acids such as sulfonic acids or carboxylic acids, for example trichloroacetic acid or trifluoromethanesulfonic acid. It is also possible to employ mixtures.

The proton donors which are particularly preferably employed are p-toluenesulfonic acid or sulfamic acid or mixtures thereof.

The proton donor can be employed in amounts of from 0.05 to 0.6 equivalent, preferably 0.1 to 0.5 equivalent, based on the compound II.

The reaction takes place in the presence of a polar organic solvent, and examples of suitable solvents are dimethyl sulfoxide, dimethylformamide, N,N'-dimethylimidazolidinone and ethylene glycol, and aprotic polar solvents are preferred. N-Methylpyrrolidone (NMP) is employed as the particularly preferred solvent.

It is advisable to employ the solvent in amounts such that the required product can be crystallized directly out of the reaction mixture in good yield and high purity without the need to remove the solvent by distillation beforehand in order to concentrate the reaction mixture.

From 150 to 250 ml of solvent are preferably added per mole of compound II.

The solid starting materials can be introduced into the reaction vessel and then the solvent can be added.

The mixture is then heated to temperatures in the range from 170 to 190° C., preferably 175 to 180° C. This results in a clear solution.

The process is generally carried out under atmospheric pressure. However, elevated pressures may also be advisable.

The reaction time depends on the amounts employed. The end of the reaction can be determined by HPLC analysis.

The reaction mixture is then cooled to temperatures in the region of 130° C., and water is added to the reaction mixture. This results in two phases. The phase separation is then carried out at 90 to 100° C.

The amount of water added is chosen so that two phases are formed with the reaction mixture. The amount may differ depending on the organic solvent used.

In the case of NMP, sufficient water is preferably added for the ratio of NMP to water to be 1:1.5 to 1:3, particularly preferably 1:1.8 to 1:2.3.

The upper phase is cooled further, with crystal formation starting in the region of 65° C. Cooling is continued to temperatures of 10±5° C., it being advisable to stir the mass of crystals.

The crystals can then be removed by filtration with suction and washed with cold water. The crystalline product can then be dried in vacuo.

The crude product obtained in this way generally has purities of >90% by weight.

If a greater purity is required, the product can be recrystallized from a suitable solvent (mixture). Examples of suitable solvents are acetonitrile/water mixtures.

The imidazolidinone is prepared using a distinctly simplified process with an improved purity and yield in the modified preparation process.

It is advantageous inter alia that evolution of ammonia is virtually completely avoided. There is likewise a marked reduction in sublimation of urea, as occurs on reaction in the melt.

The high purity of the crude product means that further recrystallization is usually unnecessary.

EXAMPLES

General Method

Preparation of
1,5-dimethyl-4-phenylimidazolidin-2-one 1 mol of an ephedrine, 1.025 mol of ammonium sulfamate, 3 mol of urea and the proton-donating compound were introduced into 200 ml of NMP. The reaction mixture was heated to 175 to 180° C. and stirred at this temperature for 2.5 h. It was then cooled to 130° C. and, at this temperature, water was added dropwise to the reaction mixture. Two phases formed. The lower phase was removed at 95° C. The upper phase was further cooled initially to 65° C. Crystals formed at this temperature. It was cooled further to 10° C. and stirred at this temperature for 1 h. The crystals were filtered off with suction and washed twice with cold water. The solid was dried in vacuo at RT overnight.

The purity of the crystalline product was determined by HPLC.

Further details are to be found in the following table.

| Example No. | | Proton donor | Water [ml] | Yield [% of th.] | Content [wt. %] |
|---|---|---|---|---|---|
| 1 | (−)-Ephedrine | 10 mol % p-Tos-OH | 360 | 56 | 98.2 |
| 2 | (+)-Ephedrine | 10 mol % p-Tos-OH | 560 | 65 | 96.4 |
| 3 | (+)-Ephedrine x HCl | 10 mol % p-Tos-OH | 360 | 63 | 98.1 |
| 4 | (+)-Ephedrine x HCl | 10 mol % sulfamic acid | 360 | 72 | 98.9 |
| 5 | (−)-Ephedrine | 50 mol % sulfamic acid | 360 | 72 | 98.6 |
| 6 | (+)-Ephedrine x HCl | 10 mol % p-Tos-OH 40 mol % sulfamic acid | 360 | 76 | 98.5 |
| 7 | (−)-Ephedrine | 10 mol % sulfamic acid | 360 | 70 | 99.6 |
| 8 | (+)-Ephedrine | 10 mol % sulfamic acid | 360 | 67 | 96.5 |
| 9 | (+)-Ephedrine x HCl | — | 360 | 71 | 99.4 |

Comparative Example 1

As Disclosed in WO 01/04098

1 eq of (−)-ephedrine, 3 eq of urea and 1.025 eq of ammonium sulfamate were introduced into 0.410 l of toluene in a stirred reactor. The mixture was heated to reflux and the solvent was distilled out. The remaining melt was then heated at 175 to 180° C. for 1.5 h. Marked evolution of ammonia and sublimation of urea ere observed. The reaction mixture was worked up by cooling the reaction mixture to 105° C. and adding 0.31 l of water. It was cooled further to 57° C., and 0.034 l of ethanol was added to the reaction mixture. It was subsequently stirred at room temperature for 4 h, and the solid was then filtered off. The solid was washed again with water and then dried at RT in vacuo under 15 mbar for 14 h. A crude product was obtained in a yield of 69%. The purity of the crude product was 84% by weight.

The crude product was recrystallized from a water/acetonitrile mixture. Purities of >98% by weight were achieved thereafter, with the yield for the crystallization being 75%, corresponding to an overall yield of 49%.

Comparative Example 2

(+)-Ephedrine hydrochloride was reacted in analogy to comparative example 1. The crude yield was 59%, with a purity of 78% by weight.

We claim:

1. A process for preparing chiral imidazolidin-2-ones of the general formula I

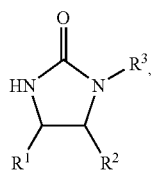

(I)

in which

R$^1$ is C$_1$-C$_8$-alkyl, cyclohexyl, phenyl, a C$_1$-C$_6$-alkyl-, halo-, nitro-, C$_1$-C$_6$-alkoxy-, C$_1$-C$_6$-alkylmercapto- or CF$_3$-substituted phenyl radical, naphthyl or a C$_1$-C$_6$-alkyl-, halo-, nitro-, C$_1$-C$_6$-alkoxy- or CF$_3$-substituted naphthyl radical, R$_2$ is C$_1$-C$_8$-alkyl, C$_2$-C$_8$-alkenyl, cyclohexyl, phenyl or a phenyl-C$_1$-C$_6$-alkyl radical which may be substituted by a nitro, C$_1$-C$_6$-alkoxy, methylenedioxy or CF$_3$ radical, and R$_3$ is C$_1$-C$_{12}$-alkyl, C$_2$-C$_8$-alkenyl, cyclohexyl, phenyl or a C$_1$-C$_6$-alkyl-, halo-, nitro-, C$_1$-C$_6$-alkoxy-, methylenedioxy-, dialkylamino- or CF$_3$-substituted phenyl radical, by reacting a compound of the formula II or the salt thereof

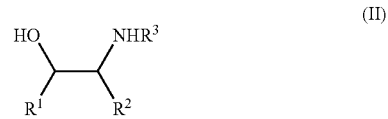

(II)

in which R$^1$, R$^2$ and R$^3$ have the abovementioned meaning, with urea in the presence of an ammonium salt, wherein the reaction is carried out in the presence of a polar organic solvent and the reaction takes place in solution at temperatures of from 170 to 190° C., and wherein the reaction is carried out in the presence of proton donors, wherein an acid with a pKa of ≦3 is used as proton donor.

2. A process as claimed in claim 1, wherein an aprotic solvent is used.

3. A process as claimed in claim 1, wherein N-methylpyrrolidone is employed as organic solvent.

4. A process as claimed in claim 1, wherein R$^1$ is phenyl and R$^2$ and R$^3$ are methyl.

5. A process as claimed in claim 1, wherein para-toluenesulfonic acid is employed as proton donor.

6. A process as claimed in claim 1, wherein sulfamic acid is employed as proton donor.

7. A process as claimed in claim 1, wherein the proton donor is employed in amounts of from 0.05 to 0.6 equivalent based on the compound of the formula II.

8. A process as claimed in claim 1, wherein (1S,2R)-ephedrine or a salt thereof is employed as compound of the formula II.

9. A process as claimed in claim 1, wherein (1R,2S)-ephedrine or a salt thereof is employed as compound of the formula II.

* * * * *

UNITED STATES PATENT AND TRADEMARK OFFICE
CERTIFICATE OF CORRECTION

PATENT NO. : 7,365,210 B2  Page 1 of 1
APPLICATION NO. : 10/510439
DATED : April 29, 2008
INVENTOR(S) : Ernst et al.

It is certified that error appears in the above-identified patent and that said Letters Patent is hereby corrected as shown below:

In Claim 1, col. 6, indicated line 1:
"$R_2$" should read --$R^2$--

In Claim 1, col. 6, indicated line 5:
"$R_3$" should read --$R^3$--

Signed and Sealed this

Fifteenth Day of July, 2008

JON W. DUDAS
*Director of the United States Patent and Trademark Office*